(12) United States Patent
Trieu et al.

(10) Patent No.: US 8,118,840 B2
(45) Date of Patent: Feb. 21, 2012

(54) VERTEBRAL ROD AND RELATED METHOD OF MANUFACTURE

(75) Inventors: Hai H. Trieu, Cordova, TN (US); Carlos Gil, Collierville, TN (US); Rodney Ballard, Lakeland, TN (US); Julien Prevost, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 351 days.

(21) Appl. No.: 12/394,363

(22) Filed: Feb. 27, 2009

(65) Prior Publication Data

US 2010/0222818 A1 Sep. 2, 2010

(51) Int. Cl.
*A61B 17/70* (2006.01)

(52) U.S. Cl. .................................................... 606/254

(58) Field of Classification Search ........... 606/246–279
See application file for complete search history.

(56) References Cited

U.S. PATENT DOCUMENTS

| | | | |
|---|---|---|---|
| 4,743,260 A | 5/1988 | Burton | |
| 5,047,055 A | 9/1991 | Bao et al. | |
| 5,092,866 A | 3/1992 | Breard et al. | |
| 5,180,393 A | 1/1993 | Commarmond | |
| 5,258,043 A | 11/1993 | Stone | |
| 5,282,863 A | 2/1994 | Burton | |
| 5,365,996 A | 11/1994 | Crook | |
| 5,375,823 A | 12/1994 | Navas | |
| 5,415,661 A | 5/1995 | Holmes | |
| 5,423,816 A | 6/1995 | Lin | |
| 5,480,401 A | 1/1996 | Navas | |
| 5,540,688 A | 7/1996 | Navas | |
| 5,556,687 A | 9/1996 | McMillin | |
| 5,562,737 A | 10/1996 | Graf | |
| 5,584,834 A | 12/1996 | Errico et al. | |
| 5,645,599 A | 7/1997 | Samani | |
| 5,672,175 A | 9/1997 | Martin | |
| 5,704,936 A | 1/1998 | Mazel | |
| 5,733,284 A | 3/1998 | Martin | |
| 5,961,516 A | 10/1999 | Graf | |
| 5,993,448 A | 11/1999 | Remmler | |
| 6,146,419 A | 11/2000 | Eaton | |
| 6,241,730 B1 | 6/2001 | Alby | |
| 6,248,106 B1 | 6/2001 | Ferree | |
| 6,267,764 B1 | 7/2001 | Elberg | |
| 6,293,949 B1 | 9/2001 | Justis et al. | |
| 6,296,643 B1 | 10/2001 | Hopf et al. | |
| 6,383,221 B1 | 5/2002 | Scarborough et al. | |
| 6,402,750 B1 | 6/2002 | Atkinson et al. | |
| 6,440,169 B1 | 8/2002 | Elberg et al. | |
| 6,616,669 B2 | 9/2003 | Ogilvie et al. | |
| 6,626,904 B1 | 9/2003 | Jammet et al. | |
| 6,645,207 B2 | 11/2003 | Dixon et al. | |
| 6,706,044 B2 | 3/2004 | Kuslich et al. | |
| 6,761,719 B2 | 7/2004 | Justis et al. | |
| 6,783,527 B2 | 8/2004 | Drewry et al. | |
| 6,786,930 B2 | 9/2004 | Biscup | |

(Continued)

*Primary Examiner* — Eduardo C Robert
*Assistant Examiner* — Summer Kostelnik (57) ABSTRACT

A vertebral rod includes a first elongated section, a second elongated section and an intermediate section disposed between the first section and the second section. The intermediate section has an inner surface and opposing end portions that define an open portion. A removable element extends from one of the first, second or intermediate sections and is disposable adjacent the opposing end portions. The element is configured to prevent engagement of the opposing end portions. A resistance member is configured for disposal with the intermediate section and engaging at least a portion of the inner surface. A method of manufacture is also disclosed.

8 Claims, 4 Drawing Sheets

U.S. PATENT DOCUMENTS

| | | |
|---|---|---|
| 6,835,205 B2 | 12/2004 | Atkinson et al. |
| 6,966,910 B2 | 11/2005 | Ritland |
| 6,986,771 B2 | 1/2006 | Paul et al. |
| 6,989,011 B2 | 1/2006 | Paul et al. |
| 6,991,632 B2 | 1/2006 | Ritland |
| 7,018,379 B2 | 3/2006 | Drewry et al. |
| 7,029,475 B2 | 4/2006 | Panjabi |
| 7,066,957 B2 | 6/2006 | Graf |
| 7,083,621 B2 | 8/2006 | Shaolian et al. |
| 7,083,622 B2 | 8/2006 | Simonson |
| 7,125,410 B2 | 10/2006 | Freudiger |
| 7,137,985 B2 | 11/2006 | Jahng |
| 7,229,441 B2 | 6/2007 | Trieu et al. |
| 7,282,065 B2 | 10/2007 | Kirschman |
| 7,285,121 B2 | 10/2007 | Braun et al. |
| 7,291,150 B2 | 11/2007 | Graf |
| 7,297,146 B2 | 11/2007 | Braun et al. |
| 7,326,210 B2 | 2/2008 | Jahng et al. |
| 7,329,258 B2 | 2/2008 | Studer |
| 7,335,200 B2 | 2/2008 | Carli |
| 7,338,525 B2 | 3/2008 | Ferree |
| 7,361,196 B2 | 4/2008 | Fallin et al. |
| 7,377,921 B2 | 5/2008 | Struder et al. |
| 7,476,238 B2 | 1/2009 | Panjabi |
| 7,556,639 B2 | 7/2009 | Rothman et al. |
| 7,559,942 B2 | 7/2009 | Paul et al. |
| 7,578,849 B2 | 8/2009 | Trieu |
| 7,601,166 B2 | 10/2009 | Biedermann et al. |
| 7,604,653 B2 | 10/2009 | Kitchen |
| 7,604,654 B2 | 10/2009 | Fallin et al. |
| 2002/0133155 A1 | 9/2002 | Ferree |
| 2003/0109880 A1 | 6/2003 | Shirado et al. |
| 2003/0114853 A1 | 6/2003 | Burgess et al. |
| 2003/0171749 A1 | 9/2003 | Le Couedic et al. |
| 2003/0220643 A1 | 11/2003 | Ferree |
| 2004/0002708 A1 | 1/2004 | Ritland |
| 2004/0006343 A1 | 1/2004 | Sevrain |
| 2004/0015166 A1 | 1/2004 | Gorek |
| 2004/0049189 A1 | 3/2004 | Le Couedic et al. |
| 2004/0049190 A1 | 3/2004 | Biedermann et al. |
| 2004/0143264 A1 | 7/2004 | McAfee |
| 2004/0147928 A1 | 7/2004 | Landry et al. |
| 2004/0172024 A1 | 9/2004 | Gorek |
| 2004/0215192 A1 | 10/2004 | Justis et al. |
| 2004/0267260 A1 | 12/2004 | Mack et al. |
| 2005/0049708 A1 | 3/2005 | Atkinson et al. |
| 2005/0055244 A1 | 3/2005 | Mullan et al. |
| 2005/0065515 A1 | 3/2005 | Jahng |
| 2005/0065516 A1 | 3/2005 | Jahng |
| 2005/0085814 A1 | 4/2005 | Sherman et al. |
| 2005/0085815 A1 | 4/2005 | Harms et al. |
| 2005/0113927 A1 | 5/2005 | Malek |
| 2005/0124991 A1 | 6/2005 | Jahng |
| 2005/0131407 A1 | 6/2005 | Sicvol et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0154390 A1 | 7/2005 | Biedermann et al. |
| 2005/0165396 A1 | 7/2005 | Fortin et al. |
| 2005/0171540 A1 | 8/2005 | Lim et al. |
| 2005/0171543 A1 | 8/2005 | Timm et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0182400 A1 | 8/2005 | White |
| 2005/0182401 A1 | 8/2005 | Timm et al. |
| 2005/0182409 A1 | 8/2005 | Callahan et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203519 A1 | 9/2005 | Harms et al. |
| 2005/0209694 A1 | 9/2005 | Loeb |
| 2005/0261685 A1 | 11/2005 | Fortin et al. |
| 2005/0261686 A1 | 11/2005 | Paul |
| 2005/0277922 A1 | 12/2005 | Trieu et al. |
| 2005/0277934 A1 | 12/2005 | Vardiman |
| 2005/0288670 A1 | 12/2005 | Panjabi et al. |
| 2005/0288672 A1 | 12/2005 | Ferree |
| 2006/0004367 A1 | 1/2006 | Alamin et al. |
| 2006/0009768 A1 | 1/2006 | Ritland |
| 2006/0009846 A1 | 1/2006 | Trieu et al. |
| 2006/0036240 A1 | 2/2006 | Colleran et al. |
| 2006/0064090 A1 | 3/2006 | Park |
| 2006/0084982 A1 | 4/2006 | Kim |
| 2006/0084984 A1 | 4/2006 | Kim |
| 2006/0084987 A1 | 4/2006 | Kim |
| 2006/0084991 A1 | 4/2006 | Borgstrom et al. |
| 2006/0089645 A1 | 4/2006 | Eckman |
| 2006/0142758 A1 | 6/2006 | Petit |
| 2006/0142760 A1 | 6/2006 | McDonnell |
| 2006/0184171 A1 | 8/2006 | Biedermann et al. |
| 2006/0189985 A1 | 8/2006 | Lewis |
| 2006/0195093 A1 | 8/2006 | Jahng |
| 2006/0212033 A1 | 9/2006 | Rothman et al. |
| 2006/0229608 A1 | 10/2006 | Foster et al. |
| 2006/0247632 A1 | 11/2006 | Winslow et al. |
| 2006/0247637 A1 | 11/2006 | Colleran et al. |
| 2006/0264935 A1 | 11/2006 | White |
| 2006/0264937 A1 | 11/2006 | White |
| 2006/0271048 A1 | 11/2006 | Thramann |
| 2006/0276247 A1 | 12/2006 | Martinez |
| 2006/0276790 A1 | 12/2006 | Dawson et al. |
| 2006/0282080 A1 | 12/2006 | Albert et al. |
| 2006/0293657 A1 | 12/2006 | Hartmann |
| 2007/0005062 A1 | 1/2007 | Lange et al. |
| 2007/0016190 A1 | 1/2007 | Martinez et al. |
| 2007/0016193 A1 | 1/2007 | Ritland |
| 2007/0016200 A1 | 1/2007 | Jackson |
| 2007/0016201 A1 | 1/2007 | Freudiger |
| 2007/0043356 A1 | 2/2007 | Timm et al. |
| 2007/0049936 A1 | 3/2007 | Colleran et al. |
| 2007/0049937 A1 | 3/2007 | Matthis et al. |
| 2007/0055247 A1 | 3/2007 | Jahng |
| 2007/0073289 A1 | 3/2007 | Kwak et al. |
| 2007/0088359 A1 | 4/2007 | Woods et al. |
| 2007/0100341 A1 | 5/2007 | Reglos et al. |
| 2007/0118122 A1 | 5/2007 | Butler et al. |
| 2007/0123865 A1 | 5/2007 | Schlapfer et al. |
| 2007/0123871 A1 | 5/2007 | Jahng |
| 2007/0129729 A1 | 6/2007 | Petit et al. |
| 2007/0191832 A1* | 8/2007 | Trieu ............................. 606/61 |
| 2007/0191846 A1 | 8/2007 | Bruneau et al. |
| 2007/0198088 A1 | 8/2007 | Biedermann et al. |
| 2007/0213719 A1 | 9/2007 | Hudgins et al. |
| 2007/0225710 A1 | 9/2007 | Jahng et al. |
| 2007/0233064 A1 | 10/2007 | Holt |
| 2007/0270838 A1 | 11/2007 | Bruneau et al. |
| 2007/0270860 A1 | 11/2007 | Jackson |
| 2007/0276380 A1 | 11/2007 | Jahng et al. |
| 2007/0276500 A1 | 11/2007 | Zucherman et al. |
| 2007/0288008 A1 | 12/2007 | Park |
| 2007/0288093 A1 | 12/2007 | Le Couedic et al. |
| 2007/0293862 A1 | 12/2007 | Jackson |
| 2008/0021459 A1 | 1/2008 | Lim |
| 2008/0027549 A1 | 1/2008 | Kirschman |
| 2008/0033435 A1 | 2/2008 | Studer et al. |
| 2008/0039943 A1 | 2/2008 | Le Couedic |
| 2008/0045951 A1 | 2/2008 | Fanger et al. |
| 2008/0065071 A1 | 3/2008 | Park |
| 2008/0097431 A1 | 4/2008 | Vessa |
| 2008/0097434 A1 | 4/2008 | Moumene et al. |
| 2008/0140076 A1 | 6/2008 | Jackson |
| 2008/0140122 A1 | 6/2008 | Bethell |
| 2008/0147122 A1 | 6/2008 | Jackson |
| 2008/0154307 A1 | 6/2008 | Colleran et al. |
| 2008/0161854 A1 | 7/2008 | Bae et al. |
| 2008/0172091 A1 | 7/2008 | Anderson |
| 2008/0177316 A1 | 7/2008 | Bergeron et al. |
| 2008/0177317 A1 | 7/2008 | Jackson |
| 2008/0177320 A1 | 7/2008 | McBride |
| 2008/0177329 A1 | 7/2008 | Perez-Cruet et al. |
| 2008/0177331 A1 | 7/2008 | Perez-Cruet et al. |
| 2008/0183212 A1 | 7/2008 | Veldman et al. |
| 2008/0183213 A1 | 7/2008 | Veldman et al. |
| 2008/0215094 A1 | 9/2008 | Taylor |
| 2008/0221620 A1 | 9/2008 | Krause |

| | | |
|---|---|---|
| 2008/0234739 A1 | 9/2008 | Hudgins et al. |
| 2008/0234744 A1 | 9/2008 | Zylber et al. |
| 2008/0255617 A1 | 10/2008 | Cho et al. |
| 2008/0262554 A1 | 10/2008 | Hayes et al. |
| 2008/0294195 A1 | 11/2008 | Egli et al. |
| 2008/0294197 A1 | 11/2008 | Egli et al. |
| 2008/0300633 A1 | 12/2008 | Jackson |
| 2008/0306450 A1 | 12/2008 | Martin |
| 2008/0306451 A1 | 12/2008 | Woehr et al. |
| 2008/0306452 A1 | 12/2008 | Crawford |
| 2008/0312694 A1 | 12/2008 | Peterman et al. |
| 2008/0319482 A1 | 12/2008 | Jackson |
| 2008/0319486 A1 | 12/2008 | Hestad et al. |
| 2009/0005817 A1 | 1/2009 | Friedrich et al. |
| 2009/0012562 A1 | 1/2009 | Hestad et al. |
| 2009/0030465 A1 | 1/2009 | Altarac et al. |
| 2009/0048631 A1 | 2/2009 | Bhatnagar et al. |
| 2009/0054932 A1 | 2/2009 | Butler et al. |
| 2009/0093819 A1 | 4/2009 | Joshi |
| 2009/0093845 A1 | 4/2009 | Hestad et al. |
| 2009/0093846 A1 | 4/2009 | Hestad |
| 2009/0099606 A1 | 4/2009 | Hestad et al. |
| 2009/0099607 A1 | 4/2009 | Fallin et al. |
| 2009/0105762 A1 | 4/2009 | Jackson |
| 2009/0112265 A1 | 4/2009 | Hudgins et al. |
| 2009/0118767 A1 | 5/2009 | Hestad et al. |
| 2009/0131981 A1 | 5/2009 | White |
| 2009/0163953 A1 | 6/2009 | Biedermann et al. |
| 2009/0163955 A1 | 6/2009 | Moumene et al. |
| 2009/0171395 A1 | 7/2009 | Jeon et al. |
| 2009/0192548 A1 | 7/2009 | Jeon et al. |
| 2009/0228043 A9 | 9/2009 | Egli et al. |
| 2009/0228044 A1 | 9/2009 | Jeon et al. |
| 2009/0228045 A1 | 9/2009 | Hayes et al. |

* cited by examiner

VERTEBRAL ROD AND RELATED METHOD OF MANUFACTURE

TECHNICAL FIELD

The present disclosure generally relates to medical devices for the treatment of spinal disorders, and more particularly to a vertebral rod configured to provide structural and dimensional stability during manufacturing and assembly thereof.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders include discectomy, laminectomy, fusion and implantable prosthetics. As part of these surgical treatments, connecting elements such as vertebral rods are often used to provide stability to a treated region. During surgical treatment, one or more rods may be attached to the exterior of two or more vertebral members.

Rods redirect stresses away from a damaged or defective region while healing takes place to restore proper alignment and generally support the vertebral members. In some applications, rods are attached to the vertebral members without the use of implants or spinal fusion. Flexible connecting elements are also known that permit limited spinal motion of a spinal motion segment. Such flexible connecting elements can provide dynamic spinal support.

Vertebral rods and their component parts can be manufactured employing, for example, molds, dies, machining and extrusion methods. In some cases, these manufacturing methods can undesirably alter the shape and/or dimension of the contemplated rod design. For example, during manufacture employing injection molding, the molded part can suffer from warping, shrinkage and creep.

Therefore, it would be desirable to provide a vertebral rod configured to provide structural and dimensional stability during manufacturing and assembly of the vertebral rod and its component parts. Desirably, the vertebral rod includes a stability element, at least a portion of which being removable from the vertebral rod, which avoids undesirable or unintended alteration of rod shape and dimension to preserve the integrity of the vertebral rod design. It would also be desirable if such a vertebral rod system includes a guide element to facilitate assembly of components of the vertebral rod.

SUMMARY OF THE INVENTION

Accordingly, a vertebral rod configured to provide structural and dimensional stability during manufacturing and assembly of the vertebral rod and its component parts is provided. Desirably, the vertebral rod includes a stability element, at least a portion of which being removable from the vertebral rod, which avoids undesirable or unintended alteration of rod shape and dimension to preserve the integrity of the vertebral rod design. It is contemplated that such a vertebral rod includes a guide element to facilitate the assembly of components of a vertebral rod.

In one embodiment, the vertebral rod includes a transitional, posterior pedicle-based device. The transitional device is a posterior pedicle screw based system for the lumbar spine. The transitional device has a rod with an offset intermediate section having a C-shape configured for disposal of a bumper of elastic compressible material, such as polyurethane or silicone. Alternatively, the vertebral rod can be lordotically curved to match the anatomy of a patient and extended to fixate multiple spinal segments.

The transitional device may be inserted bilaterally such that a first transitional device is attached on the left side pedicles and a second transitional device is attached on the right side pedicles. Among other things, the transitional device provides stability in the application of flexion and extension forces from the body to the transitional devices, as well as lateral bending motion.

The bumper may have different sizes, shapes and material properties to provide a desired amount of distraction and dampening.

In another embodiment, the transitional device includes a temporary structural or nonstructural element configured to provide, among other things, stability and/or to facilitate bumper assembly during manufacture, which may include injection molding and assembly. The temporary element is removable. For example, the temporary element provides stability to the transitional device after insertion of the bumper. In one embodiment, the temporary element with the transitional device includes an elliptical element bridging across an opening of the C-section of the transitional device. This configuration prevents unintended closing of the C-section during the manufacturing process. In another embodiment, the temporary element is a post attached to a mid-portion of an inner surface of the C-section. The post extends out beyond the opening of the C-section to guide the insertion of the bumper with the transitional device. The post is also configured to prevent unintended closing or collapse of the opening of the C-section during the manufacturing process. At least a portion of the post is removable following insertion of the bumper with the transitional device.

In another alternate embodiment, the vertebral rod includes a pedicle screw based transitional rod having a C-shaped intermediate section having an opening, with a bumper disposed therein to provide dampening and avoid an engagement of the opening faces of the C-shape intermediate section, which could result in a hard stop engagement or impact of the faces. The transitional rod is molded with an elliptical shaped element configured to avoid collapse of the C-shaped intermediate section. Alternatively, an interference post/element may be employed to avoid collapse of the C-shaped intermediate section. This configuration avoids, among other things, possible drawbacks that can be associated with manufacturing, which can undesirably affect rod shape and dimension. This configuration further facilitates manufacture and assembly of the rod by guiding the bumper with the intermediate section.

In an alternate embodiment, the temporary element includes a bridge configured to prevent closing and/or collapse of an opening of the intermediate section. The bridge can have a U shaped geometric configuration. Alternatively, the bridge can have other geometric configurations such as C, V and W.

The temporary bridge provides, among other things, structural and dimensional stability during manufacturing. The temporary bridge may be injection-molded, machined or could be a second component added as part of the manufacturing process. The temporary bridge is configured and disposed with the transitional device to maintain stability, preserve the integrity of the transitional device by preventing closure and/or collapse of an opening of the intermediate section of the transitional device. This configuration avoids the drawbacks associated with manufacture of the transitional device that can undesirably alter rod shape and dimension such as warping, shrinking and creep, which may occur prior to insertion of the bumper.

Desirably, the bridge prevents closing of the opening of the intermediate section while allowing expansion of the opening to allow insertion of the bumper and thereby facilitate assembly of the transitional device.

It is contemplated that at least a portion of the bridge is removable by clipping or machining the bridge from the transitional device after the bumper is assembled with the transitional device. The bumper provides support and/or stability to the transitional device in place of the bridge prior to removal.

In one particular embodiment, in accordance with the principles of the present disclosure, a vertebral rod is provided. The vertebral rod includes a first elongated section, a second elongated section and an intermediate section disposed between the first section and the second section. The intermediate section has an inner surface and opposing end portions that define an open portion. A removable element extends from one of the first, second or intermediate sections and is disposable adjacent the opposing end portions. The element is configured to prevent engagement of the opposing end portions. A resistance member is configured for disposal with the intermediate section and engaging at least a portion of the inner surface.

The removable element may extend from the opposing end portions. The removable element may alternatively extend from a first opposing end portion to a second opposing end portion of the opposing end portions and include an arcuate section. The removable element can have an elliptical configuration.

In an alternate embodiment, the intermediate section has a C-shaped configuration defining a correspondingly shaped inner surface, whereby the removable element is further configured to prevent collapse of the intermediate section.

In another embodiment, the removable element is an elongated post. The post may be configured as a guide for receiving the resistance member to facilitate assembly of the resistance member with the intermediate section. A portion of the removable element can be removed such that a remaining portion of the removable element is disposed between the opposing end portions. The post can extend from the inner surface of the intermediate section. The removable element may extend from one of the first or second sections and is movable relative thereto for disposal and removal from the open portion. The removable element can have an arcuate configuration.

In another alternate embodiment, the vertebral rod includes a first elongated section and a second elongated section including at least a portion thereof having an arcuate configuration that defines a radius of curvature. A flexible intermediate section is disposed between the first section and the second section. The intermediate section has an inner surface that defines a cavity and opposing first and second end portions that define an open end. A removable, arcuate bridge extends from the open end in a configuration to prevent engagement of the first and second end portions. A bumper is disposed within the cavity such that the bumper is fixed with the intermediate section.

The bridge can have an elliptical configuration wherein the intermediate section has a C-shaped configuration defining a correspondingly shaped inner surface, whereby the bridge is further configured to prevent collapse of the intermediate section. The second section may define a radius of curvature in a range of 20-400 mm.

In another alternate embodiment, a method of manufacturing a vertebral rod for a vertebral rod system is provided. The method includes the steps of providing a vertebral rod, similar to those described herein; providing a resistance member; assembling the resistance member with the intermediate section such that the resistance member is disposed within a cavity defined by the inner surface of the intermediate section; and removing at least a portion of the removable element from the vertebral rod.

The step of assembling may further include guiding the resistance member along the removable element, such as a post, into the cavity.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

The exemplary embodiments of the vertebral rod and methods of use, manufacture and assembly disclosed are discussed in terms of medical devices for the treatment of spinal disorders and more particularly, in terms of a vertebral rod configured to provide structural and dimensional stability during manufacture and assembly of the vertebral rod and its component parts. It is envisioned that the vertebral rod includes a stability element, at least a portion of which being removable from the vertebral rod, which avoids undesirable or unintended alteration of rod shape and dimension to preserve the integrity of the vertebral rod design. It is envisioned that the vertebral rod of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is further envisioned that the vertebral rod of the present disclosure may be employed with surgical treatments including open surgery and minimally invasive procedures, of such disorders, such as, for example, discectomy, laminectomy, fusion, bone graft and implantable prosthetics. It is contemplated that the vertebral rod of the present disclosure may be employed with other osteal and bone related applications, including those associated with diagnostics and therapeutics. It is further contemplated that the disclosed vertebral rod may be employed in a surgical treatment with a patient in a prone or supine position, employing a posterior, lateral or anterior approach. The present disclosure may also be employed with procedures for treating the lumbar, cervical, thoracic and pelvic regions of a spinal column.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The following discussion includes a description of a vertebral rod, related components and exemplary methods of manufacture and assembly of the vertebral rod in accordance with the principles of the present disclosure. Alternate embodiments are also disclosed. Reference will now be made in detail to the exemplary embodiments of the present disclosure, which are illustrated in the accompanying figures. Turning now to FIGS. 1-4A, there is illustrated components of a vertebral rod 20 in accordance with the principles of the present disclosure.

The components of vertebral rod 20 are fabricated from materials suitable for medical applications, including metals, polymers, ceramics, biocompatible materials and/or their composites, depending on the particular application and/or preference of a medical practitioner. For example, vertebral rod 20 can be fabricated from materials such as titanium, thermoplastics such as polyaryletherketone (PAEK) including PEEK and PEK, carbon-PEEK composites, PEEK-BaSO$_4$ polymeric rubbers, biocompatible materials such as polymers including plastics, metals, ceramics and composites thereof, rigid polymers including polyphenylene, polyamide, polyimide, polyetherimide, polyethylene, epoxy; and different sections of the rod may have alternative material composites to achieve various desired characteristics such as strength, rigidity, elasticity, compliance, biomechanical performance, durability and radiolucency or imaging preference. As a further example, a resistance member of the vertebral rod system may be fabricated from materials such as silicone, polyurethane, silicone-polyurethane, copolymers, polymeric rubbers, polyolefin rubbers, hydrogels, semi-rigid and rigid materials, and biocompatible materials such as elastomers, rubbers, thermoplastic elastomers, thermoset elastomers, elastomeric composites and plastics. One skilled in the art, however, will realize that such materials and fabrication methods suitable for assembly and manufacture, in accordance with the present disclosure, would be appropriate.

Vertebral rod 20 is configured for attachment to vertebrae (not shown) as, for example, part of a vertebral rod system during surgical treatment of a spinal disorder. See, for example, U.S. patent application Ser. No. 12/192,606 the contents of which being incorporated by reference herein in its entirety, which describes exemplary vertebral rod systems and surgical treatments. Vertebral rod 20 includes a first elongated section, such as, for example, upper section 22 that defines a longitudinal axis a. A second elongated section, such as, for example, lower section 24 defines a longitudinal axis b.

Upper section 22 has a first length and lower section 24 has a second, greater length. In a first orientation of vertebral rod 20, longitudinal axis a is disposed at an angle of 180 degrees relative to longitudinal axis b. Lower section 24 has an arcuate configuration and an increased length providing the ability to extend over two or more intervertebral elements of a spine (not shown). It is contemplated that the configuration of the vertebral rod system may provide dynamic or flexible stabilization over a plurality of intervertebral levels, including treated and untreated vertebral and intervertebral levels. It is envisioned that lower section 24 may be attached with vertebrae across lower lumbar levels such as levels L5-S1. Lower section 24 may be cut or trimmed during a surgical procedure such that the size of vertebral rod 20 can be modified according to patient needs or the particular requirements of a surgical treatment or medical practitioner.

The arcuate configuration of lower section 24 has a radius of curvature $r_1$. Desirably, the radius of curvature $r_1$ is in a range of 20-400 mm, preferably in a range of 50-200 mm, and most preferably in a range of 100-150 mm. In an alternate embodiment, upper section 22 can have an arcuate configuration and/or an increased length, similar to that described. An arcuately configured upper section 22 has a radius of curvature including those ranges discussed herein. It is contemplated that an arcuately configured section 22 may have an equivalent or non-equivalent radius, same or alternate orientation relative to lower section 24.

An intermediate section 26 is connected with sections 22, 24 and disposed therebetween as a joining section of the components of vertebral rod 20. It is envisioned that the components of vertebral rod 20 may be monolithically formed, integrally connected or arranged with attaching elements. Intermediate section 26 is flexible relative to sections 22, 24, and is configured to provide resistance to movement of sections 22, 24. Section 22 may have a different cross-sectional area, geometry, material or material property such as strength, modulus or flexibility relative to section 24. It is envisioned that the cross-sectional geometry or area of intermediate section 26 can be uniform, non-uniform, consistent or variable.

Intermediate section 26 may have one or a plurality of elements connecting sections 22, 24 such as spaced apart portions, staggered patterns and mesh. Intermediate section 26 may be fabricated from the same or alternative material to sections 22, 24. Intermediate section 26 may be connected to sections 22, 24 using various methods and structure including molding of a continuous component, mechanical fastening, adhesive bonding and combinations thereof. It is envisioned that intermediate section 26 has a flexible hinge configuration, which can be offset forward or backward relative to a central axis of rod 20 to modify flexibility or stiffness.

Figures 1, 2:
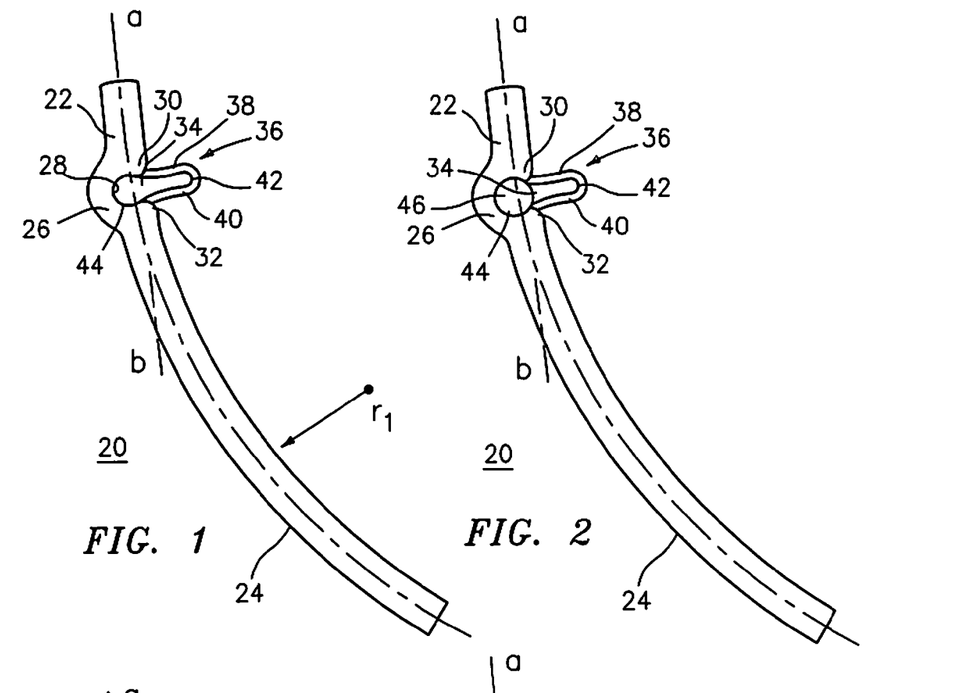
FIG. 1 is a side view of one particular embodiment of a vertebral rod in accordance with the principles of the present disclosure illustrating manufacture.
FIG. 2 is a side view of the vertebral rod shown in FIG. 1, illustrating manufacture.
Figures 3, 4, 4A:
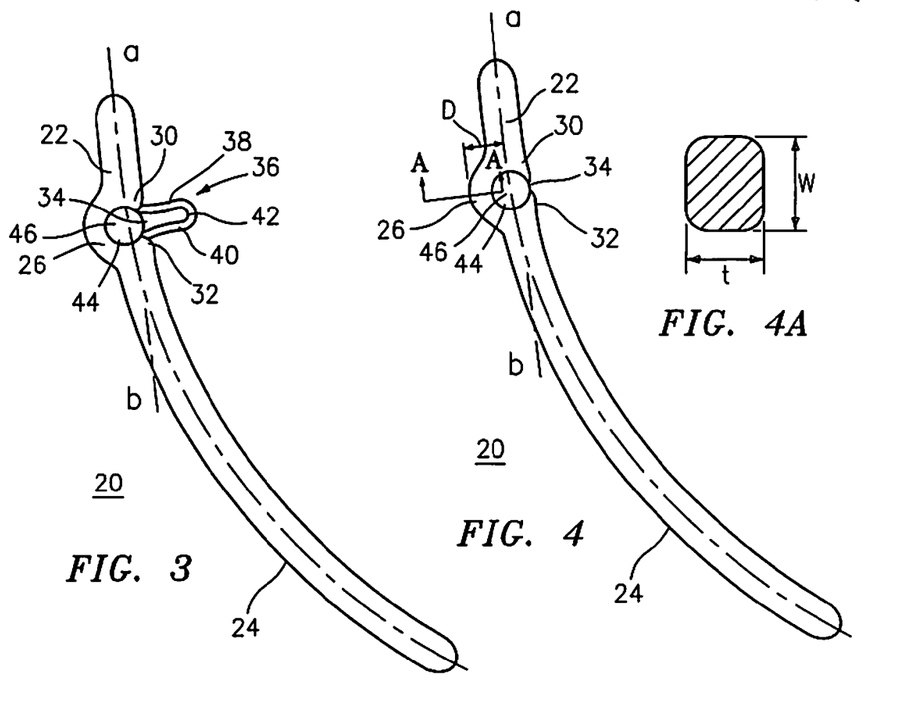
FIG. 3 is a side view of the vertebral rod shown in FIG. 2, illustrating manufacture.
FIG. 4 is a side view of the vertebral rod shown in FIG. 3, illustrating manufacture.
FIG. 4A is a cross-section view of the vertebral rod taken along line A-A of FIG. 4.

Intermediate section 26 has a depth D and a thickness t of the C-shaped configuration. Depth D, thickness t and the selected material properties of vertebral rod 20 define an allowable range of motion, for example, flexion/extension, axial compression and lateral bending of rod 20. It is envisioned that depth D is in a range of 2 mm to 30 mm. It is further envisioned that thickness t is in a range of 1 mm to 7.2 mm. In one embodiment, depth D equals 9 mm and thickness t equals 3 mm. This configuration provides an approximate flexion/extension of 4° relative to longitudinal axis a. A Width W and thickness t of the C-shaped configuration, as shown in FIG. 4A, and the selected material properties of rod 20 provide resistance of rod 20 with respect to shear and axial rotation of a spinal segment. It is envisioned that width W is in a range of 2 mm to 15 mm. It is further envisioned that thickness t is in a range of 1 mm to 7.2 mm. In one embodiment, width W equals 9 mm and thickness t equals 3 mm. This configuration provides a fatigue resistance of 225N.

Intermediate section 26 has a C-shaped configuration and defines a corresponding shaped arcuate inner surface 28. Intermediate section 26 also defines opposing end portions, such as, for example, a first opposing end portion 30 and a second opposing end portion 32. Opposing end portions 30, 32 define an open portion of intermediate section 26, such as, for example, open end 34. It is contemplated that intermediate section 26 may have alternative configurations such as U-shaped, V-shaped or W-shaped. It is further contemplated that vertebral rod 20 may include one or a plurality of intermediate sections 26 spaced along the length of rod 20. In embodiments including a plurality of sections 26, the multiple sections 26 may be disposed in similar, or alternative orientations such as aligned, non-aligned, offset, open end facing or not facing vertebrae and alternate angular orientation.

A removable element, such as, for example, arcuate bridge 36 extends from open end 34, adjacent opposing end portions 30, 32. Bridge 36 includes a first lateral section 38 extending from first opposing end portion 30 and a second lateral section 40 extending from second opposing end portion 32. First lateral section 38 and second lateral section 40 are connected with an arcuate section 42. Sections 38, 40, 42 are orientated in a substantially elliptical configuration from open end 34. It is contemplated that sections 38, 40 may be arcuate, converging, non-converging, parallel or substantially engaging. Sections 38, 40 may also be alternatively configured or have alternate thickness or materials of fabrication. It is contemplated that bridge 36 may have alternative configurations such as C-shaped, U-shaped, V-shaped or W-shaped.

Bridge 36 is configured to resist movement of intermediate section 26 and prevent engagement of first opposing end portion 30 with second opposing end portion 32. As such, bridge 36 resists movement of intermediate section 26 due, for example, to relative bending of sections 22, 24, 26 and/or manufacturing drawbacks, such as warping, shrinkage and creep. This design provides, for example, stability to the rod 20 shape and dimension to preserve integrity of the rod 20 configuration.

It is envisioned that the removable element may be configured to extend from one or more of sections 22, 24 and 26. It is further envisioned that rod 20 may include one or a plurality of removable elements. It is contemplated that the removable element prevents collapse of section 26.

Inner surface 28 of intermediate section 26 defines a cavity 44, which is configured for disposal of a resistance member, such as, for example, a bumper 46. Bumper 46 is fixedly mounted with intermediate section 26.

Bumper 46 is elastic and configured to provide variable resistance to movement of sections 22, 24 and 26 during use of vertebral rod 20. Bumper 46 is disposed within cavity 44 and engages inner surface 28 in a close fitting engagement. It is contemplated that the resiliency of bumper 46 can prevent creep and improve shape recovery of vertebral rod 20. It is envisioned that bumper 46 can be configured to prevent and/or resist closing of open end 34. Bumper 46 can be inserted with cavity 44 for assembly, or formed in situ by, for example, a pouch, bag or balloon with the bumper configuration being inserted into cavity 44 and injected with a curable material.

In manufacture and assembly, a vertebral rod, similar to vertebral rod 20 described with regard to FIGS. 1-4, is formed and assembled with other components as part of a vertebral rod system according to the requirements of a particular treatment of a spinal disorder. It is contemplated that vertebral rod 20 and its related component parts can be manufactured employing, for example, molds, dies, machining and extrusion methods.

For example, vertebral rod 20 can be fabricated employing a method of manufacturing via injection molding. Rod 20 is formed with bridge 36, described above, in a configuration to resist movement of intermediate section 26 and prevent engagement of first opposing end portion 30 and second opposing end portion 32. As such, bridge 36 resists movement of intermediate section 26 caused by relative bending of sections 22, 24, 26 and undesirable manufacturing effects such as warping, shrinkage and creep. This configuration of molded rod 20 provides, among other things, stability to rod 20 and avoids unintended and/or undesirable alteration of rod 20 shape and dimension to preserve integrity of the rod design. For example, undesirable or unintended alteration of rod 20 can be avoided during removal of the molded rod part from the mold and thereafter as the molded rod part cools. It is contemplated that bridge 36 prevents closing of open end 34 while allowing expansion of open end 34 to facilitate assembly of bumper 46 with intermediate section 26.

Bumper 46 is assembled with intermediate section 26 such that bumper 46 is disposed within cavity 44. It is envisioned that bumper 46 can be inserted with cavity 44 for assembly, or formed in situ as described. It is contemplated that a pin may be inserted with rod 20.

Bridge 36 is removed from vertebral rod 20 adjacent opposing end portions 30, 32 and discarded. Vertebral rod 20 is prepared for application with a treatment for a spinal disorder. It is contemplated that bridge 36 may be removed via clipping or machining. Vertebral rod 20 can be used with various bone screws, pedicle screws or multi-axial screws (MAS) used in spinal surgery. It is contemplated that vertebral rod 20 may be used with pedicle screws coated with an osteoconductive material such as hydroxyapatite and/or osteoinductive agent such as a bone morphogenic protein for enhanced bony fixation to facilitate motion of the treated spinal area. Rod 20 and bumper 46 can be made of radiolucent materials such as polymers. Radiomarkers may be included for identification under x-ray, fluoroscopy, CT or other imaging techniques. Metallic or ceramic radiomarkers, such as tantalum beads, tantalum pins, titanium pins, titanium end caps and platinum wires can be used with rod 20 and its related components.

Figure 5:
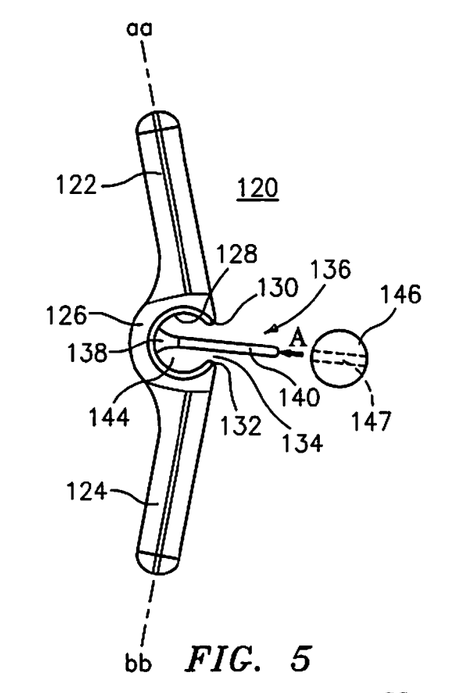
FIG. 5 is a side view of an alternate embodiment of the vertebral rod shown in FIGS. 1-4, illustrating manufacture.
Figure 6:
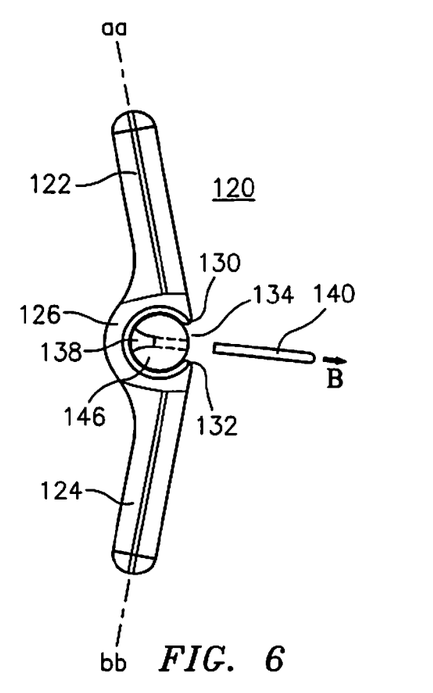
FIG. 6 is a side view of the vertebral rod shown in FIG. 5, illustrating manufacture.
Figure 7:
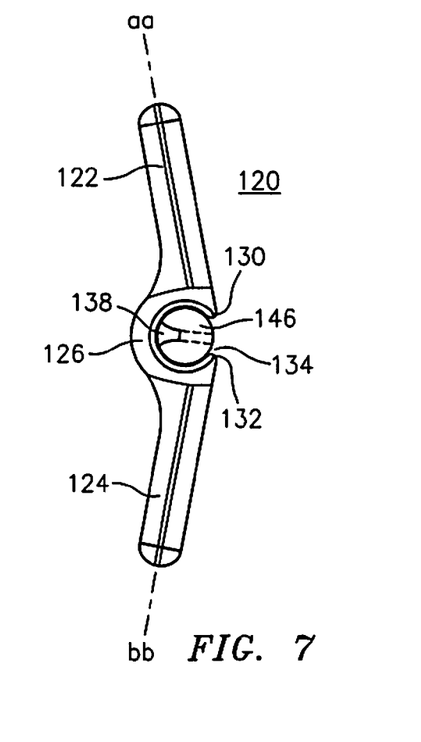
FIG. 7 is a side view of the vertebral rod shown in FIG. 6, illustrating manufacture.

Referring to FIGS. 5-7, in an alternate embodiment of a vertebral rod in accordance with the principles of the present disclosure, similar to vertebral rod 20 described with regard to FIGS. 1-4, a vertebral rod 120 is provided.

Vertebral rod 120 includes an upper section 122 that defines a longitudinal axis aa. A lower section 124 defines a longitudinal axis bb. It is contemplated that the length of upper section 122 and lower section 124 are substantially equivalent. It is further contemplated that sections 122, 124 may be alternately configured and dimensioned.

An intermediate section 126 is connected with sections 122, 124 and disposed therebetween as a joining section of the components of vertebral rod 120. Intermediate section 126 has a C-shaped configuration and defines a corresponding shaped arcuate inner surface 128. Intermediate section 126 defines a first opposing end portion 130 and a second opposing end portion 132. Opposing end portions 130, 132 define open end 134.

A removable element, such as, for example, an elongated post 136 extends through open end 134, adjacent opposing end portions 130, 132 and disposed therebetween. Elongated post 136 is configured to prevent engagement of first opposing end portion 130 with second opposing end portion 132. As such, elongated post 136 resists movement of intermediate section 126 due, for example, to relative bending of sections 122, 124, 126 and/or manufacturing drawbacks, such as warping, shrinkage and creep. This design provides, for example, stability to the rod 120 shape and dimension to preserve integrity of the rod 120 configuration.

Elongated post 136 includes a first section 138 extending from inner surface 128 and a second, removable section 140 extending from first section 138. Second section 140 is removable from first, remaining section 138 during manufacture, as will be described. It is contemplated that second section 140 may be joined to first section 138 by a reduced thickness portion such that second section 140 is frangible from first section 138 by pulling or tearing therefrom, or alternatively may be removed from first section 138 via machining or clipping. Sections 138, 140 may be alternatively configured or have alternate thickness or materials of fabrication. It is contemplated that elongated post 136 prevents collapse of section 126.

Inner surface 128 of intermediate section 126 defines a cavity 144, which is configured for disposal of a bumper 146. Bumper 146 is fixedly mounted with intermediate section 126.

Vertebral rod 120, similar to the method of manufacture and assembly of vertebral rod 20 described with regard to FIGS. 1-4, is formed and assembled with other components as part of a vertebral rod system according to the requirements of a particular treatment of a spinal disorder. Vertebral rod 120 is fabricated via injection molding and is formed with elongated post 136, described above, in a configuration to prevent engagement of first opposing end portion 130 and second opposing end portion 132.

As such, elongated post 136 resists undesired movement of intermediate section 126 caused by relative bending of sections 122, 124, 126 and undesirable manufacturing effects such as warping, shrinkage and creep. This configuration of molded rod 120 provides, among other things, stability to rod 120 and avoids unintended and/or undesirable alteration of rod 120 shape and dimension to preserve integrity of the rod design. It is contemplated that elongated post 136 prevents closing of open end 134 while allowing expansion of open end 134 to facilitate assembly of bumper 146 with intermediate section 126.

During the step of assembly of bumper 146 with vertebral rod 120, bumper 146 is provided with an elongated cavity 147 configured for slidable reception of post 136. Post 136 is configured as a guide such that bumper 146 passes therealong via cavity 147, as shown by arrow A in FIG. 5. As such, bumper 146 is assembled with intermediate section 126 and disposed within cavity 144. Upon disposal of bumper 146 within cavity 144, second section 140 is removed from first section 138, as described above, as shown by arrow B in FIG. 6, and discarded. As assembled, first section 138 remains with intermediate section 126 and is disposed in only a portion of cavity 147. Vertebral rod 120 is prepared for application with a treatment for a spinal disorder.

Figure 8:
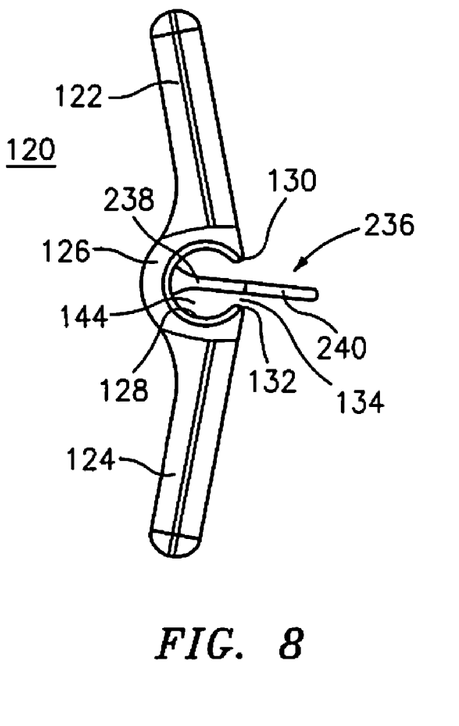
FIG. 8 is a side view of an alternate embodiment of the vertebral rod shown in FIG. 5, illustrating manufacture.
Figure 9:
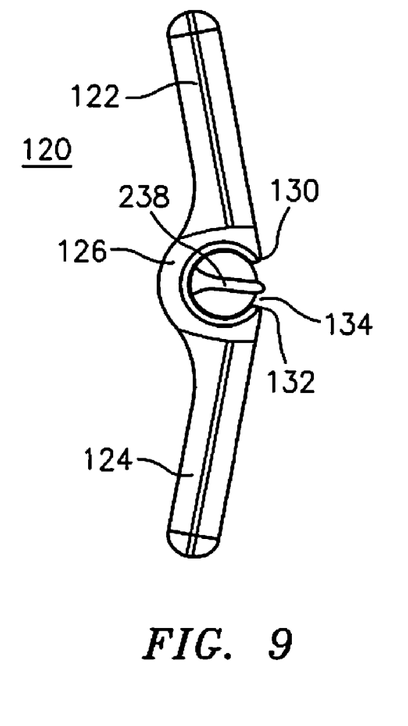
FIG. 9 is a side view of the vertebral rod shown in FIG. 8, illustrating manufacture.

In an alternate embodiment, as shown in FIGS. 8-9, similar to that described with regard to FIGS. 5-7, vertebral rod 120 includes an elongated post 236, similar to post 136, which extends through open end 134, adjacent opposing end portions 130, 132 and disposed therebetween.

Elongated post 236 includes a first section 238 extending from inner surface 128 and a second, removable section 240 extending from first section 238. Second section 240 is removable from first, remaining section 238 during manufacture, as described above.

During the step of assembly of bumper 146 with vertebral rod 120, bumper 146 is provided with elongated cavity 147 (FIG. 5) configured slidable reception of post 236. Post 236 is configured as a guide such that bumper 146 passes therealong via cavity 147. Upon disposal of bumper 146 within cavity 144, second section 240 is removed from first section 238, as described above and discarded. As assembled, first section 238 remains with intermediate section 126 and is disposed such that first section 238 completely occupies cavity 147, as shown in FIG. 9. Vertebral rod 120 is prepared for application with a treatment for a spinal disorder.

Figure 10:
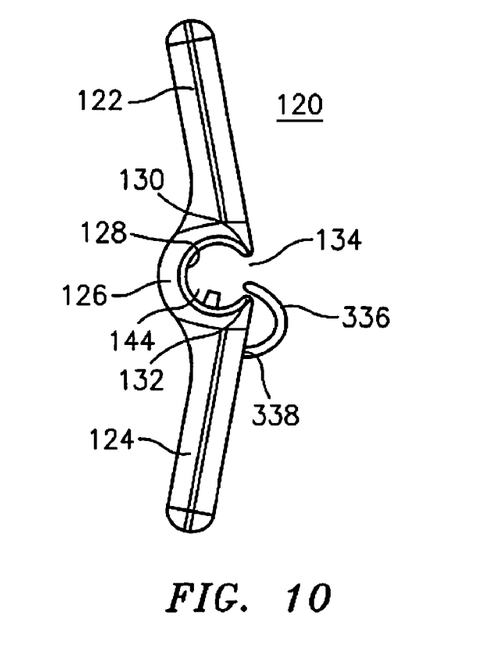
FIG. 10 is a side view of another alternate embodiment of the vertebral rod shown in FIG. 5, illustrating manufacture.
Figure 11:
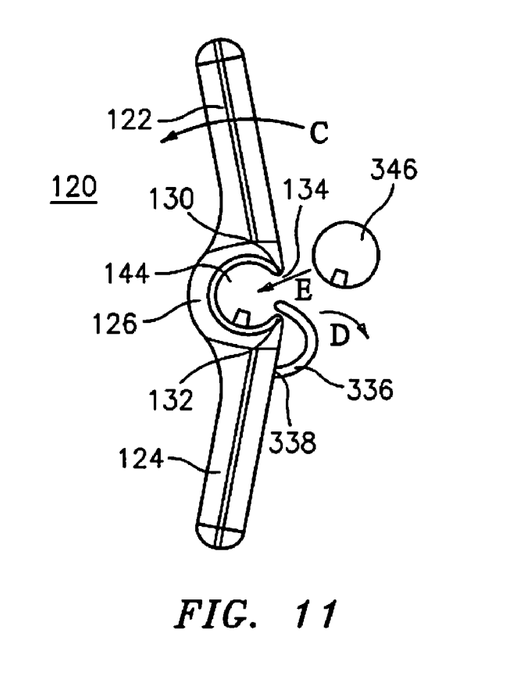
FIG. 11 is a side view of the vertebral rod shown in FIG. 10, illustrating manufacture.
Figure 12:
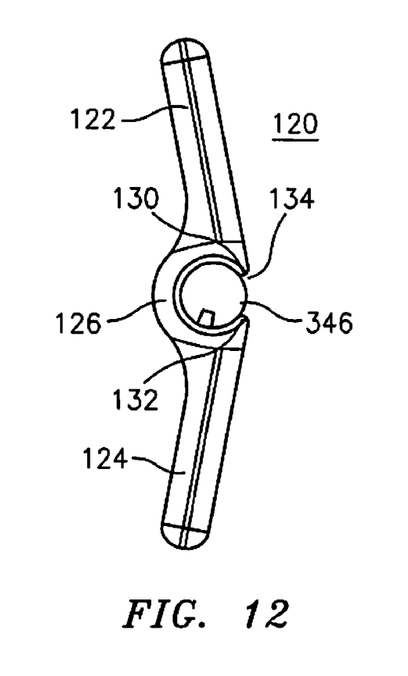
FIG. 12 is a side view of the vertebral rod shown in FIG. 11, illustrating manufacture.

In another alternate embodiment, as shown in FIGS. 10-12, similar to that described with regard to FIGS. 5-7, vertebral rod 120 includes a removable element, post 336, extending from lower section 124 and pivotally movable relative thereto. Post 336 extends through open end 134, adjacent opposing end portions 130, 132 and disposed therebetween.

Post 336 is configured to prevent engagement of first opposing end portion 130 with second opposing end portion 132. As such, post 336 resists movement of intermediate section 126 due, for example, to relative bending of sections 122, 124, 126 and/or manufacturing drawbacks, such as warping, shrinkage and creep. This design provides, for example, stability to the rod 120 shape and dimension to preserve integrity of the rod 120 configuration.

Post 336 includes an end 338 connected to lower section 124 and extends therefrom in an arcuate configuration for disposal between opposing end portions 130, 132. End 338 is removable from lower section 124 during manufacture, as will be described. It is contemplated that end 338 may be joined to lower section 124 by a reduced thickness portion such that end 338 is frangible from lower section 124 by pulling or tearing therefrom, or alternatively may be removed from lower section 124 via machining or clipping. It is contemplated that post 336 prevents collapse of section 126. It is envisioned that post 336 is injection molded with rod 120.

Inner surface 128 of intermediate section 126 defines a cavity 144, which is configured for disposal of a bumper 346. Bumper 346 is fixedly mounted with intermediate section 126.

Post 336 resists undesired movement of intermediate section 126 caused by relative bending of sections 122, 124, 126 and undesirable manufacturing effects such as warping, shrinkage and creep. This configuration of molded rod 120 provides, among other things, stability to rod 120 and avoids unintended and/or undesirable alteration of rod 120 shape and dimension to preserve integrity of the rod design. It is contemplated that post 336 prevents closing of open end 134 while allowing expansion of open end 134 to facilitate assembly of bumper 346 with intermediate section 126.

During the step of assembly of bumper 346 with vertebral rod 120, upper section 122 is rotated, as shown by arrow C in FIG. 11, to expand open end 134. Post 336 is rotated relative to lower section 124, as shown by arrow D in FIG. 11, such that bumper 346 is free to pass through open end 134, as shown by arrow E in FIG. 11. As such, bumper 346 is assembled with intermediate section 126 and disposed within cavity 144. Upon disposal of bumper 146 within cavity 144, post 336 is removed from lower section 124, as described above, and discarded. Vertebral rod 120 is prepared for application with a treatment for a spinal disorder.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A vertebral rod comprising:
   a first elongated section;
   a second elongated section;
   an intermediate section disposed between the first section and the second section, the intermediate section having an inner surface and opposing end portions that define an open portion;
   a post extending from the intermediate section at a point between the end portions and extending through the open portion; the element configured to prevent abutment of the opposing end portions;
   a resistance member disposed in the intermediate section and engaging at least a portion of the inner surface;
   wherein the post extends into the resistance member.

2. A vertebral rod according to claim 1, wherein the post extends entirely through the resistance member.

3. A vertebral rod comprising:
   a first elongated section;
   a second elongated section;
   an intermediate section disposed between the first section and the second section, the intermediate section having an inner surface and opposing end portions that define an open portion;
   a post extending from the intermediate section at a point between the end portions and extending through the open portion; the element configured to prevent abutment of the opposing end portions;
   a resistance member disposed in the intermediate section and engaging at least a portion of the inner surface;
   wherein the post comprises a first post section mounted to the intermediate section and a second post section attached to the first post section and disposed sequentially relative thereto; wherein the rod is changeable from a first configuration wherein the resistance member is disposed around both the first and second post sections and the first post section is joined to the second post section and a second configuration wherein the resistance member is disposed around the first post section and the second post section is disjoined from the first post section.

4. A vertebral rod comprising:
   a first elongated section;
   a second elongated section;
   an intermediate section disposed between the first section and the second section, the intermediate section having an inner surface and opposing end portions that define a gap;
   a removable element extending from one of the first or second sections and into the gap in spaced relation to the end portions of the intermediate portion such that a free end portion of the removable element is disposed directly between the end portions of the intermediate section;
   a resistance member being disposable in the intermediate section so as to engage at least a portion of the inner surface.

5. A vertebral rod according to claim 4 wherein the element has an arcuate configuration.

6. A method of manufacturing a vertebral rod for a vertebral rod system, the method comprising the steps of:
   providing a vertebral rod, the vertebral rod including:
      a first elongated section;
      a second elongated section;
      an intermediate section disposed between the first and second sections; the intermediate section having an inner surface and opposing end portions that define a gap,
      a bridge element distinct from the first section, second section, and intermediate section; the bridge element disposed adjacent the opposing end portions so as to enclose the gap when the rod is free of externally applied loads; the element being configured to prevent engagement of the opposing end portions;
   providing a resistance member;
   assembling the resistance member with the intermediate section such that the resistance member is disposed within a cavity defined by the inner surface of the intermediate section; and
   thereafter, removing the bridge element from between the opposing end portions.

7. A method of manufacturing a vertebral rod according to claim 6 wherein the intermediate section has a C-shaped configuration defining a correspondingly shaped inner surface; wherein the bridge element is further configured to prevent collapse of the intermediate section.

8. A method of manufacturing a vertebral rod for a vertebral rod system, the method comprising steps of:
   providing a vertebral rod, the vertebral rod including:
      a first elongated section;
      a second elongated section;
      an intermediate section disposed between the first section and the second section, the intermediate section having an inner surface and opposing end portions that define an open portion;
      an element extending from one of the first, second and intermediate sections and being disposable adjacent the opposing end portions; the element being configured to prevent engagement of the opposing end portions; wherein the element is an elongated post extending from the inner surface of the intermediate section through the open portion;
   providing a resistance member;
   assembling the resistance member with the intermediate section such that the resistance member is disposed within a cavity defined by the inner surface of the intermediate section; wherein the step of assembling further includes guiding the resistance member along the post into the cavity;
   removing at least a portion of the element in the vertebral rod.

* * * * *